United States Patent [19]

Shell et al.

[11] Patent Number: 4,478,818
[45] Date of Patent: Oct. 23, 1984

[54] OCULAR PREPARATION HOUSING STEROID IN TWO DIFFERENT THERAPEUTIC FORMS

[75] Inventors: John W. Shell, Hillsborough; Robert M. Gale, Mountain View, both of Calif.

[73] Assignee: Alza Corporation, Palo Alto, Calif.

[21] Appl. No.: 568,480

[22] Filed: Jan. 5, 1984

Related U.S. Application Data

[60] Division of Ser. No. 453,358, Dec. 27, 1982, Pat. No. 4,432,964, which is a continuation of Ser. No. 295,653, Aug. 24, 1981, abandoned, which is a division of Ser. No. 196,608, Oct. 14, 1980, Pat. No. 4,304,765.

[51] Int. Cl.$^3$ .................. A61K 9/00; A61K 9/26; A61K 31/565; A61K 31/74
[52] U.S. Cl. ...................... 424/14; 424/16; 424/19; 424/22; 424/28; 424/75; 424/238; 424/239; 424/240; 424/241; 424/242; 424/243
[58] Field of Search ............ 424/14, 16, 19–22, 424/28, 238–243

[56] References Cited

U.S. PATENT DOCUMENTS

| | | | |
|---|---|---|---|
| 2,932,606 | 4/1960 | Shull et al. | 167/65 |
| 2,978,379 | 4/1961 | Shell | 167/58 |
| 3,073,743 | 1/1963 | Spero | 167/65 |
| 3,105,795 | 10/1963 | Nobile | 167/65 |
| 3,134,718 | 5/1964 | Nobile | 167/65 |
| 3,138,527 | 6/1974 | Spero | 167/65 |
| 3,197,367 | 7/1965 | Panzarella | 167/65 |
| 3,536,809 | 10/1970 | Applezweig | 424/28 |
| 3,743,741 | 7/1973 | Laurent et al. | 424/242 |
| 3,780,176 | 12/1973 | Young | 424/239 |
| 3,863,633 | 2/1975 | Ryde et al. | 128/260 |
| 3,867,519 | 2/1975 | Michael | 424/19 |
| 3,868,445 | 2/1975 | Ryde et al. | 424/14 |
| 3,923,939 | 2/1975 | Baker et al. | 264/49 |
| 3,934,013 | 1/1976 | Poulsen | 424/239 |
| 3,961,628 | 6/1976 | Arnold | 128/260 |
| 3,962,414 | 6/1976 | Michaels | 424/19 |
| 3,968,201 | 7/1976 | Ryde et al. | 424/14 |
| 4,001,388 | 1/1977 | Shell | 424/14 |
| 4,052,505 | 10/1977 | Higuchi et al. | 424/14 |
| 4,057,619 | 11/1977 | Higuchi et al. | 424/14 |
| 4,115,544 | 9/1978 | Shell | 424/14 |
| 4,164,559 | 8/1979 | Miyata et al. | 424/14 |
| 4,177,256 | 12/1979 | Michaels et al. | 424/22 |
| 4,179,497 | 12/1979 | Cohen et al. | 424/22 |
| 4,186,184 | 1/1980 | Zaffaroni | 424/14 |
| 4,304,765 | 12/1981 | Shell et al. | 424/14 |

OTHER PUBLICATIONS

Higuchi et al., J. Pharm. Sci., vol. 52, No. 1, pp. 67–71, 1963, *Dissolution Rates of Finely Divided Powders, 1, Effect of a Distribution of Particle Sizes in a Diffusion-Controlled Process.*

Higuchi et al., J. Pharm. Sci., vol. 52, No. 2, pp. 150–159, 1963, *Polymorphism and Drug Availability, Solubility Relationships in Methylprednisolone System.*

Higuchi et al., J. Pharm. Sci., vol. 52, No. 2, pp. 162–164, 1963, *Dissolution Rates of Finely Divided Drug Powders II, Micronized Methylprednisolone.*

Haleblian et al., J. Pharm. Sci., vol. 58, No. 8, pp. 911–929, 1969, *Pharmaceutical Applications of Polymorphism.*

Haleblian et al., J. Pharm. Sci., vol. 60, No. 10, pp. 1485–1491, 1971, *Isolation and Characterization of Some Solid Phases of Fluprednisolone.*

Haleblian, J. Pharm. Sci., vol. 64, No. 8, pp. 1269–1288, 1975, *Characterization of Habits and Crystalline Modifications of Solids and Their Pharmaceutical Applications.*

Primary Examiner—Shep K. Rose
Attorney, Agent, or Firm—Paul L. Sabatine; Edward L. Mandell; Steven F. Stone

[57] ABSTRACT

An ocular insert and an ocular composition are disclosed. The insert and the composition comprises a steroid in two different forms.

6 Claims, 4 Drawing Figures

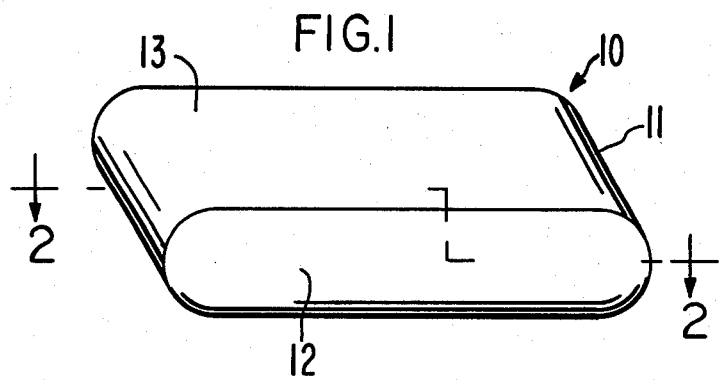
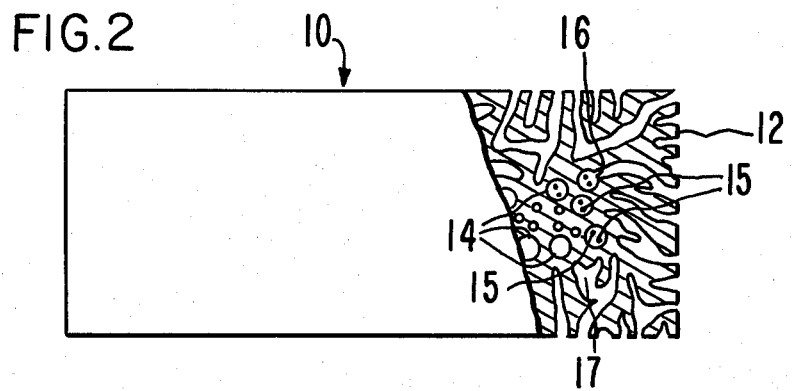
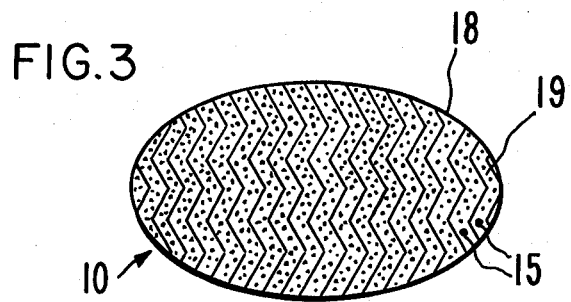
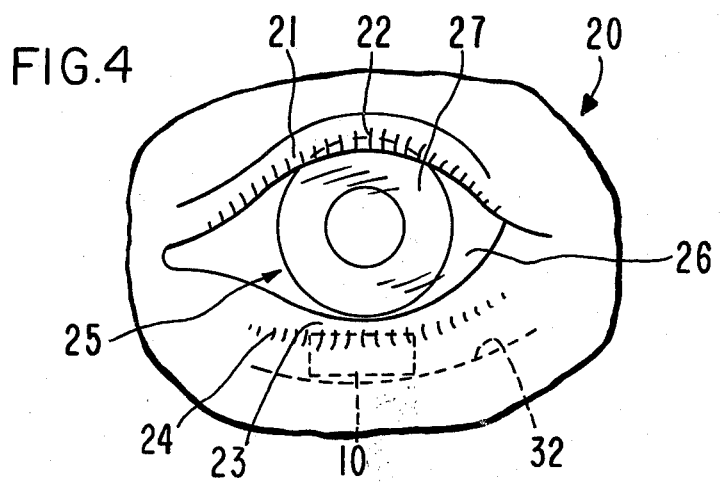

OCULAR PREPARATION HOUSING STEROID IN TWO DIFFERENT THERAPEUTIC FORMS

CROSS-REFERENCE TO RELATED APPLICATIONS

This application is a division of Ser. No. 06/453,358 filed Dec. 27, 1982 now U.S. Pat. No. 4,432,964 which is a continuation of Ser. No. 06/295,653 filed Aug. 24, 1981 now abandoned, which is a division of Ser. No. 06/196,608 filed Oct. 14, 1980 now U.S. Pat. No. 4,304,765 issured Dec. 8,1981.

FIELD OF THE INVENTION

This invention pertains to ocular pharmacology. More particularly, the invention concerns ocular preparations comprising (1) a novel and useful ocular therapeutic insert that houses and delivers the same steroid in two different forms, and (2) a novel and useful ocular pharmaceutical composition comprising a steroid in two different forms. The invention also concerns a method for the management of ocular diseases comprising administering the same steroid in two different forms to the eye for treating the disease.

DESCRIPTION OF THE PRIOR ART

Diseases of the eye, in their various manifestations represent a serious problem confronting ocular medicine. The prior art is aware of the problem, and it has made available therapeutic steroids that are indicated for the management of
diseases of the eye. The steroids were administered to the eye, in a single chemical form, and usually they were administered without any apparent consideration of the pharmacokinetics of the steroid, the physical properties of the steriod, the total therapeutic needs of the patient, and the specific biological structures of the entire eye. That is, the solubility of any given steroid is limited in tear fluid, and this limits the concentration of the steroid in the fluid, and correspondingly the concentration of the steroid in the fluid influences the amount of steroid that will penetrate the eye. Yet, as previously observed, steroids are frequently administered by practitioners without considering their physical properties, their concentration in tear fluid, and their availability for penetration into the eye. See *Ocular Pharmacology*, by William H. Havener, 4th Ed., Chapter 2, pages 19 to 38, 1978, published by the C.V. Mosby Co., Saint Louis.

In the light of the above presentation it is immediately evident, a long-felt need exists in ocular pharmacology for increasing the concentration of a steroid in tear fluid, an objective which may be obtained by dissolving different forms of the same steroid in the fluid, thereby presenting an increased concentration of total steroid instantly available for penetration into the eye. The needs exist for a preparation that can house both forms without any interactions, and make them available for immediate and future use at the therapeutically effective rates to the total eye in enhanced concentration for penetration into the eye. It will be appreciated by those versed in the ocular and dispensing arts, that if an ocular therapy is provided that can simultaneously administer the same steroid in two or more diffferent forms for the management of ocular diseases, such a therapy would have a definite use and represent a substantial contribution to practicing ocular pharmacology.

OBJECTS OF THE INVENTION

Accordingly, it is an immediate object of the invention to provide a novel and useful ocular therapeutic preparation that can house and deliver the same steroid in at least two different forms to the eye for the management of diseases of the eye.

It is another immediate object of the invention to provide an ocular therapeutic insert that can house and deliver the same steroid in at least two different chemical forms to the eye for the treatment of eye disease.

It is another immediate object of the invention to provide a novel and useful pharmaceutical composition that can house and deliver the same steroid in two different forms to house the eye for the management of unwanted eye conditions.

Another object of the invention is to provide an ocular insert comprising a steroid in two forms, that on their release from the insert increase the concentration of total steroid in tear fluid and accordingly increase the amount of steroid available for penetrations into an eye.

Another object of the invention is to provide an ocular composition comprising a steroid in two different for ms, that on their release from the composition increase the concentration of steroid in tear fluid and thereby increase the concentration of steroid for passing into the eye.

Another object of the invention is to provide a method for the management of eye diseases, and more specifically eye inflammation by administering the same steroid in two different chemical forms for the treatment thereof.

These objects, as well as other objects, features and advantages of the invention, will become more readily apparent from the following detailed description, the drawings, and the accompanying claims.

SUMMARY OF THE INVENIION

This invention concerns both an ocular insert and an ocular composition. The insert and the composition comprise and they dispense the same steroid that is present in the insert and in the composition in two physically and chemically different forms. The insert and the composition dispense the steroid for the treatment of eye diseases, particularly inflammation of the eye.

BRIEF DESCRIPIION OF THE DRAWINGS

In the drawings, which are not drawn to scale, but are set forth to illustrate the invention, the Figures are as follows:

FIG. 1 is a view of an ocular insert made and used by the invention for dispensing the same steroid in two different forms from the insert at controlled rates;

FIG. 2 is a cross-sectional view of the insert of FIG. 1 taken through 2—2 thereof for illustrating the structure and operation of the insert;

FIG. 3 is a cross-sectional view of an ocular therapeutic insert housing a steroid that is released in different forms from the insert to the eye; and FIG. 4 is a partly frontal and partly diagrammatic view of a human eye illustrating an ocular therapeutic insert in operation dispensing the same steroid in two forms to the eye.

In the drawings, and in the specification, like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Turning now to the drawings in detail, which are an example of an ocular preparation manufactured as an ocular insert for dispensing a steroid, and which example is not to be construed as limiting, one insert is indicated in FIG. 1 by the numeral 10. Insert 10, is manufactured for administering a medication steroid comprising two different forms thereof, not seen in FIG. 1, to the eye, particularly the eye of warm-blooded animals. The term animal as used herein includes human. Insert 10 comprises a body 11 made of a polymeric film 12, and insert 10 has at least one surface 13 for releasing the medication steroid in its two forms to the eye.

Insert 10 is manufactured, sized, shaped, structured and adapted for easy insertion and comfortable prolonged retention in the eye. The insert can have any geometric shape, and its dimensions can vary to conform to the eye. The lower limit on the size of the insert is governed by the amount of steroid to be housed and administered to elicit the desired pharmological and ophthalmic response, as well as the smallest sized insert that can be conveniently inserted and maintained in the eye.

Insert 10 of FIG. 1 as seen in FIG. 2 in cross-section through 2—2 of FIG. 1. Insert 10 comprises a plurality of discrete depots 14 comprising therein a steroid in two forms, indicated by dots 15, which depots 14 are dispersed through a polymer matrix 12. The polymer surrounds and encloses depots 14 and binds them into a solid, unit body 11. Polymer 12 surrounds depots 14 individually so that each depot 14 is individually encapsulated by a layer of polymer 12. Polymer 12 is made of a material that is nontoxic, substantially non-erodible in the eye, impermeable to the passage of steroid 15, and it is permeable to the passage of an external fluid, that is tear fluid. Steroid 15 in depots 14 consists essentially of the two forms, with at least one steroid in this embodiment an osmotically effective solute, or the steroid in two forms and an osmagent optionally additionally present in depots 14.

In operation, when insert 10 is manufactured as an osmotic insert and in a fluid environment of use, the fluid diffuses into polymer 12 and is imbibed into depot 14 forming a solution containing steroid therein. The rate of fluid imbibition is related to the osmotic pressure gradient exhibited by the steroid and/or the osmagent across the polymer wall encapsulating depot 14 against the external fluid. As fluid is imbibed into depot 14, it continuously fills depot 14 and generates a hydrostatic pressure in depot 14. This pressure is applied against the polymer causing it to rupture and form an aperture 16, with steroid released through the aperture from depot 14, near the surface of system 10 to the eye. Steroid 15 is continuously released from system 10 by the inward progressive formation of apertures in depot 14 forming a lattice of dispensing paths 17 in polymer 12 for releasing steroid 15 from within system 10 to its exterior. The dispensing paths can have openings on all sides of system 10, they can be interconnected through tortuous paths of regular and irregular shapes discernible by microscopic examination. As fluid is imbibed into depot 14, it fills the paths, and they become a means for transporting steroid therethrough, with release occurring at a controlled and beneficial rate over a prolonged period of time from the osmotic therapeutic insert.

Turning to FIG. 3, an ocular therapeutic system 10 is seen in open section, designed for administering steroid 15 to an eye. System 10 comprises a drug delivery module 18 made of a polymeric release rate controlling material 19, preferably manufactured as a solid polymeric matrix or as a container, which matrix or container are a reservoir for housing steroid 15. In the embodiment described, the release rate controlling material is permeable to the passage of steroid 15 by diffusion, and it transfers steroid 15 to the eye at a controlled rate over a prolonged period of time.

In another embodiment, ocular therapeutic insert 10, as seen in FIG. 3, can be a bioerodible insert. Bioerodible insert 10 is formed of a bioerodible polymer that acts as a reservoir for housing steroid 15. As bioerodible insert 10 bioerodes, it releases steroid 15 at a controlled rate of release over a prolonged period of time to the eye.

Referring to FIG. 4, ocular therapuetic system 10 is seen in an eye 20 for administering steroid 15 to eye 20. Eye 20 comprises an upper eyelid 21 with eyelashes 22 at the edge of eyelid 21, and a lower eyelid 23 with eyelashes 24 at the edges of eyelid 23. Eye 20 anatomically comprises an eyeball 25 covered for the greater part of its posterior area by sclera 26 and its central area by cornea 27. Eyelids 21 and 23 are lined with an epithelial membrane, or palpebral conjunctiva, not shown in FIG. 4. The portion of palpebral conjunctiva which lines upper eyelid 21 and underlying portion of the bulbar conjunctiva define an upper cul-de-sac, not seen in FIG. 4. The portion of the palpebral conjunctiva that lines the lower eyelid 23 and the underlying portion of the bulbar conjunctiva define a lower cul-de-sac not seen in FIG. 4. Insert 10 may be shaped, sized and adapted for easy insertion and comfortable retention in any part of the eye.

The marginal outline of inset 10 can be ellipsoid, doughnut, bean, banana, circular, ring, crescent, rectangular, square, oval, tombstone, half-circle, and like geometric shapes. In cross-section, insert 10 can be convex, doubly convex, concavo-convex, and the like. When in the eye, insert 10 will tend to adapt the curvature of the part of the eye adjacent thereto. The dimensions of the ocular insert can vary wildly. The lower limit on the size of insert 10 is governed by the amount of the steroid 15 to be administered to elicit the desired pharmacologic or physiologic response, as well as the smallest sized system that can be conveniently inserted and maintained in the eye. The upper limit in the size of the insert 10 is governed by the geometric space limitations of the eye, consistent with the eye, and comfortable insertion and retention in the eye. Satisfactory results can be obtained with ocular inserts for insertion in the eye if an adult human having a length of 2 to 20 millimeters, a width of 1 to 15 millimeters, and a thickness of 0.1 to 4 mm.

DETAILED DESCRIPTION OF THE INVENTION

In accordance with the practice of this invention, it has now been surprisingly found that a steroid in two different chemical forms can be administered to the eye from an insert, or topically applied to the eye for their intended therapeutic effect. The phrase the same steroid in two different forms, as used herein, denotes naturally occurring and synthetic steroids used for treating diseases and inflammation of the eye. The term diseases of the eye includes phylctenular keratoconjunctivitis, nonpurulent conjunctivitis, vernal conjunctivitis and the like. The term inflammation of the eye includes inflammatory disorders of the lids, conjuctiva and sclera, anterior uveitis, iridocylitis, iritis, herpes zoster opthalmicus, thermal and chemical burns, and the like. The steroids embraced by the invention are the corticosteroids including the glucocorticoids, and antiinflammatory steroids related structurally more to progesterone than to corticocosteroids. The same steroid in two different forms indicates the dosage preparation comprises the same steroid present in an unsubstituted and substituted form, or present in two different substituted forms. For example, the steroid can be present as an alcohol and an organic ester, and alcohol and an inorganic ester, an alcohol and an ether, an ester and an ether, an acetal and an ester, an ester and an ester, and the like. The insert and the composition, in one embodiment, comprise the steroid in two or more different forms, such that on their release to tear fluid, the amount of one form of the steroid dissolved in the fluid is independent of the amount of a different form of the steroid already dissolved in the fluid. The steroid can be selected in hydrophilic and hydrophilic forms, in hydrophobic and hydrophobic forms, and in hydrophilic and hydrophobic forms as a means for controlling the amount of steroid in the fluid, and for controlling the amount of steroid available to the eye. In another embodiment, the steroid in two different forms can be selected from the exemplary pairs for their different lipophilic and lipophilic properties, for their lipophilic and hydrophilic properties, for their lipophilic and hydrophobic properties in the fluid and for their rates of penetration into tissues which leads to a preselected therapeutic and beneficial result.

Exemplary steroid in two forms include amcinafal or 9-fluoro-11$\beta$,16$\alpha$,17,21-tetrahydropregna-1,4-diene-3,20-cyclic-16, 17-acetal with 3-pentanone and amcinafide or 9-fluoro-11$\beta$, 16,$\alpha$17,21-tetrahydroxypregna-1,4-diene-3,2-dione cyclic 16, 17-acetal with acetophenone; a pair of steroids selected from the group consisting of betamethasone of 9-fluoro 11$\beta$,17$\alpha$21-trihydroxy-16$\beta$-methylpregna-1,4-diene-3,20-dione, betamethasone acetate, betamethasone benzoate, betamethasone dipropionate, betamethsaone valerate, and betamethasone disodium phosphate; a pair of steroid selected from the group consisting of cortisone or 17,21-dihydroxy-4-pregnene-3,11,20-trione cortisone 21 $\beta$-cyclopentane propionate, and cortisone 21-dihydrogen phosphate; chloroprednisone or 6$\alpha$-chloro-17,21-dihydroxypregna-1,4-diene-3,11,20-trione, and chloroprednisone acetate; clocortolone or 9-chloro-6$\alpha$-fluoro-11$\beta$,21-dihydroxy-16$\alpha$-methylpregna-1,4-diene-3, 20-dione, clocortolone acetate and clocortolone pivalate; dexamethasone or 9-fluoro-11$\beta$, 17,21-trihydroxy-16 -methylpregna-1,4-diene-3,20-dione, dexamethasone acetate, dexamethasone disodium phosphate and dexamethasone isonicotinate; desoximetasone or 9-fluoro-11$\beta$,21-dihydroxy-16$\alpha$-methylpregna-1,4-diene-3,20-dione, and desoximetasone hydrolyzable ester; descinolone or 9-fluoro-11$\beta$,16$\alpha$,17-trihydroxypregna-1,4-diene-3,20-dione, and descinolone acetonide; desonide or 16$\alpha$-hydroxyprednisolone-16$\alpha$,17-acetonide, and hydrolyzable esters; dichlorisone or 9,11]-dichloro-17,21-dihydroxypregna-1,4-diene-3,20-dione and dichlorisone acetate; diflu- prednate or 6$\alpha$,9-difluoro-11$\beta$,17,21-trihydroxypregna-1,4-diene-3,20-dione, and the hydrolyzable esters such as the 21-acetate and the 17-butyrate; fludrocortisone or 9$\alpha$-fluoro-17-hydroxy-corticosterone, and flurocortisone acetate; flumethasone or 6$\alpha$-fluorodexamethasone, flumethasone acetate and flumethasone pivalate; fluocortolone or 6$\alpha$-fluoro-16$\alpha$-methyl-1-dehydrocorticosterone, fluocortolone acetate and fluocortolone pivalate; flurandrenolone or 6$\alpha$-fluoro-11$\beta$,16$\alpha$,17,21-tetrahydroxyprogesterone cyclic 16,17-acetal with acetone, and the hydrolyzable esters; flucloronide or 9,11$\beta$-dichloro-6$\alpha$-fluoro 16$\alpha$,17,21-trihydroxy-pregna-1,4-dien-3,20-dionecyclic 16,17-acetal with acetone, and its esters; fluoro-metholone or 21-desoxy-6$\alpha$-methyl-9$\alpha$-fluoro-prednisolone, and fluorometholone acetate; fluprednisolone or 6$\alpha$-fluoro-1-dehydro-hydrocortisone, fluprednisolone acetate and fluprednisolone valerate; flunisolide or 6$\alpha$-fluoro-11$\beta$,16$\alpha$,17,21-tetrahydroxy-pregna-1,4-diene-3,20-dione cyclic 16,17-acetal with acetone, and flunisolide acetate; fluocinolone or 6$\alpha$,9$\alpha$-difluoro-16$\alpha$-hydroxyprednisolone-16,17 acetonide, and esters thereof; fluocinonide or 16$\alpha$,17$\alpha$-isopropylidene-6$\alpha$-fluoro-triamcinolone, 21-acetate, and 21-esters; fluperolone or 9$\alpha$-fluoro-11 ,17 ,21-trihydroxy-21methylpregna-1, 4-diene-3,20-dione, and the 21-esters such as 21-acetate; formocortal or 3-(2-chloroethoxy)-9$\alpha$-fluoro-6-formyl-11$\beta$,21-dihydroxy-16$\alpha$,17$\alpha$-isopropylidenedioxy-pregna-3,5-diene-20-one, and pharmaceutically acceptable esters thereof; hydrocortisone or 17-hydroxycorticosterone, hydrocortisone acetate, hydrocortisone cyclopentyl propionate, hydrocortisone phosphate, hydrocortisone sodium succinate, and hydrocortisone tebutate; medrysone or 6$\alpha$-methyl-11$\beta$-hydroxy-pregesterone, and esters, such as hydrocortison acetate and hydrocortisone butyrate, and hydrocortisone acetate and hydrocortisone phosphate; meprednisone or 16$\beta$-methylprednisone and 21 acetate; methly prednisolone or 6$\alpha$-methyl-11 ,17 ,21-triol-1,4-pregnadiene-3,20-dione, the 21-acetate and 21-succinate; paramethasone or 16$\alpha$-methyl-fluoro-prednisolone, the 21-acetate, and disodium phosphate; prednisolamate, or prednisolone-21-N,N-diethylglycinate, the dimethyl glycinate and the like; prednisolone or 3,20-dioxo-11, 17$\alpha$,21-trihydroxy-1,4-pregnadiene, the prednisolone-21-acetate, predisolone-21-trimethyl acetate and prednisolone-hemisuccinate; prednival or prednisolone, prednisolone phosphate sodium, and prednisolone-17-valerate, predinsolone acetate and prednisolone propionate, and prednisolone butyrate and phenylacetate; prednisone or 17$\alpha$,21-dihydroxy-pregna-1, 4-diene-3,11,20-trione and its 21-acetate; and triamcinolone or 9$\alpha$-fluoro-16$\alpha$-hydroxyprednisolone, triameinolone acetate, acetonide, triamcinolone hexacetonide and triamcinolone diacetate. The steroids are known to the prior art in *Cutting's Handbook of Pharmacology, The Actions and Uses of Drugs*, pages 348 to 364, 1979, published by Appleton-Century-Crofts, New York; and in *The Merck Index*, Ninth Edition, monograph numbers 4030, . 4031, 4061, 4074, 4075, 4077, 5689, 5980, and 6834, 1976, published by Merck & Co., Rahway. The amount of steroid housed in the depots of an osmotic insert generally is from 1 to 50% by weight, with a presently preferred range of 5 to 40% by weight of the total weight of the ocular, osmotic insert. The amount of steroid housed in an ocular insert that releases its steroid by diffusion is generally from 50 nanograms to 1 gram of steroid in each form, or from 100 nanogram to 2 grams total steroid for the diffusional insert. The ocular insert will release steroid over a prolonged period of 4 to 600 hours, with a preferred period of ophthalmic release of 8 hours to 240 hours.

Materials suitable for manufacturing the ocular inserts can be selected from naturally occurring and synthetic polymeric materials. These polymers are biologically compatible with the eye, and they form the insert without harm to the steroid. The polymers used for manufacturing osmotic inserts form the body of the insert, they are the encapsulating layer of the depot, they are substantially impermeable to the passage of steroid solute, they are permeable to the passage of biological fluid and water, and they form an aperature during operation of the insert in the eye. Procedures for ascertaining the impermeability and the permeability of polymeric films are known to the art in *Proc. Roy. Sci. London, Series A.* Vol 148 1935; *J. Pharm. Sci.,* Vol. 55, 1224 to 1229, 1966; in *Diffusion in Solids, Liquids and Gases,* by Jost, Chapter XI, 436 to 488, 1960, published by Academic Press, Inc., New York. Procedures for measuring aperture formation in osmotic inserts by the hydrostatic pressure in a depot exceeding the cohesive integrity of the polymer with the polymer opening for releasing medication formulation to the ocular environment of use, can be determined by measurements predicated on pressure-deflection and mechanical behavior measurement techniques reported in *Modern Plastics,* Vol. 41, 143 to ]44, 146 and 182, 1964; *Handbook of Common Polymers,* by Scott et al., 588 to 609, 1971, published by CRC Press, Cleveland, Ohio; in *Machine Design,* 107 to 111, 1975; in *J. Sci. Instruments,* Vol. 42, 591 to 596, 1965; and by measuring mechanical stress-strain patterns of polymers using the Instron ®Testing Machine, available from the Instron Corporation, of Canton, Massachusetts. The osmotic pressure, ATM, of the steroid solutes can be measured in a commercially available osmometer that measures the vapor pressure difference between pure water and the solution containing a solute to be analyzed, and according to standard thermodynamic principles, the vapor pressure ratio is converted into an osmotic pressure difference. An osmometer that can be used for the present measurements is identified as Model 302 B, Vapor Pressure Osmometer, manufactured by Hewlett Packard Company, Avondale, Pa.

Exemplary materials for fabricating the ocular, osmotic insert include ethylene-vinyl ester copolymers having an ester content of 4 to 80% such as ethylene-vinyl acetate copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer. Ethylene-vinyl ester copolymers including ethylene-vinyl acetate copolymers for the manufacture of diffusional ocular drug delivery devices where the drug dissolves in and passes through the polymer by diffusion is the invention of Higuchi and Hussain as disclosed and claimed in U.S. Pat. No. 4,052,505 issued on Oct. 4, 1977 and in U.S. Pat. No. 4,144,317 issued on Mar. 13, 1979, and assigned to the ALZA Corporation of Palo Alto, Calif. Solutes, as used for manufacture of ocular, osmotic inserts, do not substantially diffuse through polymer, as reported in *Biological Science, Molecules to Man,* by Welch et al., pages 157 and 158, 1968, published by Houghton Mifflin Company, Boston. Additional exemplary materials suitable for manufacturing system 10 include acrylonitrile-methyl vinyl ether, vinyl chloride-diethyl fumarate, homopolymers; and copolymers of partially hydrolyzed poly(vinyl alcohol), plasticized poly(vinyl chloride), plasticized poly(amides), poly(isoprene), poly(isobutylene), poly(ethylene), lightly cross-linked poly(vinyl pyrrolidone), vinyl-diethyl fumarate copolymers, ethylene-propylene copolymers, poly(urethanes), poly(saccharides), and the like. The polymeric materials are known in *Handbook of Common Polymers,* by Scott, et al., Sections 1 through 42, 1971, published by CRC Press, Cleveland, Ohio. Procedures for manufacturing and osmotic devices are disclosed by Michaels and Guillod in U.S. Pat. No. 4,177,256 issued on Dec. 4, 19798, and assigned to the ALZA Corporation of Palo Alto, Calif.

The diffusional ocular inserts used for the purpose of the invention can also be of any convenient shape for comfortable retention in the eye. Typical shapes include ellipsoid, bean-shaped, banana-shaped, circular-shaped, rectanular-shaped, trapezoidal shaped, doughnut-shaped inserts, and the like. In cross-section, it can be doubly convex, concavo-convex, and the like, and it will tend to conform to the configuration of the eye. The diffusional insert can be a monolith formed of a continuous film housing steroid, or it can be a container housing steroid therein. The dimensions of the diffusional device can vary with the size and shape of the insert, the amount of steroid in the reservoir, and the insert, the membrane which governs the rate of steroid to be administered, and the size of the eye. Satisfactory monolithic inserts generally have a length of 2 to 30 millimeters, a width of 1 to 15 millimeters, and a thickness of from 0.1 to 7.5 millimeters. An insert manufactured as a container, or with an internal reservoir for housing steroid therein. Generally, the diffusional insert will have a length of 4 to 20 millimeters, a width of 1 to 15 millimeters, a thickness of 1 to 5 millimeters, and a reservoir with a diameter of 1.2 to 14.8 millimeters. The diffusional insert generally will house from 50 nanograms to 2 grams of steroid, and more preferably from 1 microgram to 150 milligrams of steroid.

Material suitable for fabricating the diffusional ocular insert are the naturally occurring, and synthetic polymers that are biologically compatible with eye fluid, and eye tissues, and are essentially insoluble in ocular fluids with which the insert come in contact. The presently preferred materials are flexible, non-allergenic, inert, and are suitable for manufacturing inserts. The materials are steroid release rate controlling materials permeable to the passage of steroid by diffusion. The materials suitable for manufacturing are selected from the group consisting essentially of poly(olefins), carbohydrate-type-polymers, proteins, condensation-type polymers and organo-silicon polymers. More preferred polymers include poly(ethylene), poly(propylene), ethylene-vinyl acetate copolymer, cross-linked poly(vinyl alcohol), poly(acrylates), poly(amides), poly(esters), poly(carbonates), poly(silicones), and the like. The diffusional insert can also be manufactured from the polymers set forth supra, where the polymer permits the passage of steroid by diffusion.

The rate of release of a steroid through a polymer, that is the diffusion of steroid through a polymer forming the insert can be ascertained by techniques known to the art. The techniques include the transmission method, and the sorption-desorption method. The permeability of a material, and Fick's First Law of Diffusion are described in *Encyl. Polymer Science and Techology,* Vols. 5 and 9, pages 65 to 82 and 794 to 807, 1968, and the references cited therein; in *J. Pharm. Sci.*, Vol. 52, pages 1145 to 1149, 1963 ibids, Vol. 53, page 798 to 802, 1964; ibid, Vol. 54, pages 1459 to 1464, 1965; ibid, Vol. 55, page to 843 and 1224 to 1239, 1966; and in U.S. Pat. No. 4,014,335. Procedures for manufacturing diffusional ocular inserts are fully disclosed in U.S. Pat. No. 3,961,628, and in U.S. Pat. No. 4,052,505.

The osmagent, or osmotically effective solute that can be added to an osmotic, ocular insert as an aid for governing the rate of fluid imbibition into the insert, and the rate of steroid release from the insert include water-soluble inorganic and organic salts. Exemplary osmagents include magnesium sulfate, magnesium chloride, sodium chloride, lithium chloride, potassium sulfate, sodium carbonate, sodium sulfate, lithium sulfate, calcium bicarbonate, calcium sulfate, potassium acid phosphate, calcium lactate, magnesium succinate, tartaric acid, acetamide, choline chloride, soluble carbohydrates such as sorbitol, mannitol, raffinose, glucose, sucrose, lactose, and the like.

The pharmaceutical compositions, in a presently preferred embodiment, that are suitable for the practice of this invention, are ophthalmologically acceptable compositions. The compositions house and deliver the same steroid in two different therapeutically acceptable forms for achieving the desired therapy. Exemplary ophthalmic compositions that can be used include a member selected from the group consisting of ophthalmic solutions, ophthalmic suspensions and ophthalmic ointments. The compositions comprise the two forms of the same steroid admixed with a pharmaceutically acceptable carrier. The amount of steroid in the composition usually is about 0.001% to 30% steroid, based on the weight of the total composition, with a more preferred composition comprising 0.01% to 10% of each form of steroid. The compositions are administered as needed, for example, usually from 1 to 5 times daily to the steroid receptor eye.

The phrase phamaceutically acceptable carrier, as used herein, denotes non-toxic carriers, including ophthalmologically acceptable carriers that can form compositions containing the steroid, without effecting the steroid, are free of irritation to the eye, they are sterile and suitable for administering drug to the eye. The carrier can be an aqueous medium, including a member selected from the group consisting of water, saline, buffered solutions, and suspensions; also, the carrier can be an ointment. The term ointment as used herein includes gels, lipophilic compositions, and the like. The ophthalmic compositions can contain and antibacterial agent, a preservation agent, a stabilizing agent, a viscosity regulating agent, a surfactant, a buffer, an emulsifying agent, thickeners, oleaginous materials, an absorption enhancing agent, and the like.

Exemplary antibacterial agents include quaternary ammonium compounds such as benzalkonium chloride, berzethonium chloride, cetrimide, and cetylpyridinium chloride; mercurical agents such as phenylmercuric nitrate, phenylmercuric acetate, and thimerosol; alcoholic agents such as chlorobutanol, phenylethyl alcohol, and benzyl alcohol; antibacterial esters such as esters of para-hydroxybenzoic acid; and other antibacterial agents such as chlorhexidine, chlorocresol, polymyxin, and the like. The antibacterial agents used for the purpose of the invention are compatible with the steroid, they are non-toxic, and non-irritating to animal tissues, including the ocular environment. The ocular compositions usually contain from 0.001 percent to 4 percent of an antibacterial agent, and more preferably from 0.01 to 1 percent of said agent.

Exemplary viscosity regulating agents that can be added to ophthalmic compositions, are agents that increase the effective dwell time a composition containing the steroids remains in the eye by reducing the rate at which the composition leaves the eye. The viscosity agents also provide replacement of the mucoid layer in the eye and add to the comfort of the presence of the steroid in the eye. Typical viscosity regulating agents are preferably water soluble, and they include methyl cellulose, hydroxypropyl methyl cellulose, sodium carboxymethyl cellulose, polyvinyl alcohol, polyvinyl pyrrolidone, gelatin, polyethylene glycol, and the like. The amount of agent present in a composition is from 0.001% to 5%, and more preferably from about 0.01% to 2%.

The buffer systems used for the present purpose are buffer systems capable of maintaining the pH of the composition, generally in the range of 4.5 to 7.5. The buffer systems insure the stability of the steroid, they aid in controlling the steroid's activity, they are compatible with the steroid, and they minimize possible tissue irritation. Typical buffer forming agents include sodium phosphate, sodium biphosphate, sodium acetate, boric acid, sodium hydrogen carbonate, potassium acid phosphate, and the like. The agent sodium chloride can be added to the buffers for regulating their isotonicity, and sodium hydroxide can be used for adjusting their pH. Typical buffer systems include citric acid systems, phosphate buffer systems, isotonic boric acid systems, isotonic sodium borate, Sorensen buffer system, and the like.

The surfactants useful for the purpose of the invention are surface active agents that are suitable for therapeutic use, including ocular use, they are non-toxic, and they lower the tension at the surface contact between the tissue and the composition. Ihe amount of surfactant used is about 0.001% to 3%, and more preferably 0.01% up to 0.75%. The surfactant can be a fatty alcohol, an ester, an ether, a polymer, and the like. Typical surfactants include Pluronics, such as Pluronic F-68, Tergitol-1559, Spans and Tweens of H.L.P. value of 1 to 25, Polysorbate-80, glycol monoluarate, polyoxyethylene sorbitan monooleate, and the like. The words Pluronic, Tergitol, Span, Tween and Polysorbate are registered trademarks.

The stabilizing agents used for the present purpose include materials that stabilize the steroid against the harmful effects of oxidative decomposition, and solubilizing agents that increase the solubility of the steroid in the composition. The stabilizing agents include antioxidants such as sodium bisulfite, sodium thiosulfite, 8-hydroxy quinoline, ascorbic acid, sodium ascorbate, N-acetyl cysterine, and the like. The stabilizing agents also include chelating agents used to obviate the undesirable properties of metal ions without the necessity of stripping these ions from solution, thereby acting as a softening agent. Typical chelating agents include disodium ethylenediamine tetraacetate, also known as sodium edetate, and the like. The term stabilizing agent as used herein also includes solubilizing agents. Typical solubilizing agents include propylene glycol, polyethylene glycol, polysorbate-80, poloxalene, and the like. The amount of stabilizing and solubilizing agents used in about 0.001% to 5%, and more preferably about 0.01% to 2%. The amount of chelating agent used is about 0.001% to 1%, and more preferrably 0.01% to 0.5%.

Preservatives, generally in the range of 0.02% to 3%, and more preferrably about 0.05% to 0.5% also can be used to formulate acceptable compositions. Typical preservatives include methyl paraben, propyl paraben, and the like.

Ointments are prepared with conventional, non-toxic pharmaceutical vehicles. The vehicles include liquid petrolatum and white petrolatum in such proportions to afford an ointment of desired fluidity; emulsifying agents such as propylene glycol monostearate, non-ionic polyoxyalkylene derivatives of hexitol anhydride partial long chain fatty acid esters such as polyoxyalkylene derivatives of sorbitan monolaurate, sorbitan monopalmitate, sorbitan monostearate, sorbitan tristearate, sorbitan trioleate and the like; emulsifiers comprising a combination of glyceryl monostearate with polyoxyethylene sorbitan palmitate and an alcohol such as cetyl alcohol or stearyl alcohol; thickening agents such as monoglycerides and fatty alcohols, and fatty acid esters, which monoglycerides include glyceryl monostearate and glyceryl monopalmitate; the fatty alcohols include cetyl alcohol and stearyl alcohol; and the esters include myristyl stearate and cetyl stearate. Other oleaginous materials include glyceryl monooleate, myristyl alcohol, isopropyl palmitate, mineral oil gelled with polyethylene, and the like.

The pharmaceutical compositions also comprise the same steroid in two different chemical forms micronized and dispersed in a bioerodible polymer, which can be manufactured as a bioerodible, ocular insert, or as a bioerodible, ocular particle. The bioerodible insert, or the bioerodible particle is made from a polymer such as a polyester, a polypeptide, a polycarboxylic acid or a polyorthoester. Typical polymers include polylactic acid, polyglycolic acid, gelatin, poly(2,2-dioxy-trans-1,4-cylohexane dimethylene titrahydrofuran), polycarboxylic acid half ester of poly(vinyl methyl ether maleic acid) as the ethyl half ester, and the like. Generally the insert, or the particle will comprise 0.0]to 60 parts of steroid in two different forms, for example 0.01 to 30 parts of the same steroid in a different form, with the remainder of the insert or particle the bioerodible polymer. The insert is positioned in the eye as described supra, and the particle is administered to the eye by mixing it 1 to 50 parts of the particle with up to 100 parts of a liquid, suspension or ointment carrier. Procedures for manufacturing ocular particles are disclosed by patentee John W. Shell in U.S. Pat. Nos. 3,914,402; 4,001,388; and 4,115,544. The bioerodible polymers are disclosed by Jorge Heller, et al., in U.S. Pat. No. 3,811,444; by Higuchi, et al., in U.S. Pat. No. 3,981,303; by Zaffaroni in U.S. Pat. No. 4,186,184; and by Choi, et al., in U.S. Pat. No. 4,180,646.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in, the art in the light of the present disclosure and the accompanying claims.

EXAMPLE 1

A hydrophilic ophthalmic ointment comprising 0.25 gm of hydrocortisone sodium phosphate, 0.25 gm of hydrocortisone sodium succinate, 0.25 gm of methylparaben, 0.15 gm of propylparaben, 9.5 gm of sodium lauryl sulfate, 120 gm of propylene glycol, 250 gm of stearyl alcohol, 250 gm of white petrolatum, and 370 gm of water are formulated by first melting the stearyl alcohol and the petrolatum on a steam bath, warmed to about 75° C., followed by adding the other ingredients, previously dissolved in the water and warmed to 75° C., with stirring until the formulation congeals.

EXAMPLE 2

An ophthalmic solution, for administrable as eye drops, is prepared by mixing 0.5 gm of prednisolone sodium phosphate and 0.25 gm of prednisolone sodium succinate with up to 100 ml of Sorensen phosphate buffer solution consisting of 40 ml of monobasic sodium phosphate, 60 ml of dibasic sodium phosphate and 0.46 gm of sodium chloride to yield the solution.

EXAMPLE 3

A semisolid oleaginous ointment for ophthalmic use is prepared by heating to 110°-120° C. on a hot plate, 10% of the nonemulsifiable polymer Epolene C-10, having a mol. wt. of 8,000, and 90% of light mineral oil, with moderate stirring; and then adding 0.5 gm of triamcinolone and 0.5 gm of triamcinolone acetonide, with additional stirring until the steroids are incorporated into the ointment. The ointment is cooled by pouring it as a thin-layered film over a precooled piece of foil, to produce the intended gelled ointment.

EXAMPLE 4

An ophthalmic suspension comprising 0.25% of prednisolone acetate, 0.25% of prednisolone, 0.5% hydroxypropyl methylcellulose, (4,000), 0.1% thimersol, and 0.1% sodium phosphate is prepared by mixing the ingredients in a buffer consisting of sodium biphosphate and sodium phosphate, with hydrochloric acid used to adjust the pH, to yield the suspension. The suspension is prepared according to the procedures described in *Remington's Pharmaceutical Sciences*, 14th Ed., published by Mack Publishing Co., Easton, Penna.

EXAMPLE 5

An ophthalmic composition comprising 0.05% of micronized dexamethasone and 0.01% of micronized dexamethasone sodium phosphate is prepared by intimately blending the steroids with 0.5% of microcrystalline collagen and purified water up to 100%. The microcrystalline collagen is known in *Chem. Abst.*, Vol. 67, 91708j, 1967; ibid, Vol, 69, 60053d, 1968; and ibid, Vol, 80, 19583i, and 112672d, 1974.

EXAMPLE 6

A sterile, ophthalmic ointment is prepared by blending the same ophthalmic steroid in two different chemical forms selected from the steroids set forth supra, with chlorobutanol, white petrolatum, mineral oil, polyoxyl stearate, polyethylene glycol, nonionic lanolin, and purified water to produce the ointment.

EXAMPLE 7

An ocular medication osmotic dispensing insert comprising depots housing hydrocortisone acetate, hydrocortisone cyclopentylpropionate and osmagent sodium chloride, is manufactured by micronizing separately the steroids to a particle size of about ten microns, and the osmagent to a particle size of about 10 microns, mixing them, and then blending the mixture with a polymer. The procedure comprises placing 65 grams of ethylenevinyl acetate copolymer onto a conventional rubber mill and mill it until it is banded onto the rollers. Then 35 grams of the blend, comprising 15 grams of each steroid and 5 grams of osmagent, is added slowly over a period of several hours during which time the steroid is worked into the polymer. The steroid osmagent polymer composition is removed from the three roll mill and passed between the rolls after folding it several times. This process is repeated many times to insure a uniform dispersion of the steroid and the osmagent encapsulation in the polymer.

The composition is then comminuted in a ginder to reduce it to sections measuring about 2 mm in diameter. These sections then were fed to an injection molder, afixed with a die-mold. The mixture is then injection molded at 80° C. and 400 psi into elliptial ocular inserts 14×6×0.8 ;mm, moninal. The steroid release rate profile of the insert can be measured by shaking them in normal saline media at 37° C. At frequent intervals, the release media is changed completely, and the concentration in the media ascertained by standard UV assay.

EXAMPLE 8

An ocular dispensing diffusional insert having an elliptical shape and comprising two outer release rate controlling walls, each fused to an inner middle wall having a center area defining a space, and which middle wall extends around and interbounds the inner perimeter of two outer walls to form an ocular dispenser, having a reservoir for containing the steroids, defined by the internal surfaces of all the walls is manufactured as follows: first, a uniform wall material is formed by dissolving ethylene vinyl-acetate copolymer, having a vinyl acetate content of 40%, in methylene chloride in a concentration ratio of 20% copolymer to 80% solvent and film casting the solution onto a glass substrate. The solvent is allowed to evaporate at room temperature, and the film air dried to yield a film 1.7±0.2 mils thick. The two walls, about 16 mm×6.75 mm, are pressed from the film for use as the steroid release rate wall of the system. Next, a middle wall is prepared by mixing ethylene-vinyl acetate copolymer and a blue dye in the percent ratio of 20 to 80 to 0.1, and the ingredients mixed in a blender. The mixture is cast onto a glass surface, and the solvent evaporated at room temperature. Then, the film is warm air dried to yield a film 4.2±0.3 mils thick. Next, this film is press-cut into an ellipse having the same dimensions of the first press-cut walls. The middle wall is press-cut with the center area punched out to yield a continuous ellipse defining an opening. Then, onto one of the steroid release walls is placed a middle wall, and these two walls placed into a vacuum laminator. Next, a vacuum is pulled to 74 cm of mercury and held for three minutes. At the end of three minutes, a high flux radiant heater is positioned over the walls and heated for about 1.5 seconds, or until the temperature reaches about 70° C. At the end of the heating, a pressure head is applied to the walls and a pressure of 6.8 kg applied for 45 seconds to firmly seal the two walls, and the vacuum released.

Next, an aliquot comprising 150 mg of betamethasone acetate, 150 mg of betamethasone valerate, in a hydroxypropyl methylcellulose mineral oil carrier, is deposited into the center receiving area of the two walled laminate, and the third wall placed in contact with the middle wall. The three walls are vacuum heat laminated to yield the steroid releasing insert.

The novel ocular inserts and ocular compositions of the invention employ a unique means for ocular therapy. The ocular inserts and ocular composition can be used for the therapies disclosed in *Physician Desk Reference for Ophthalmology*, Chapter IV, 1979/80, published by Medical Economics Company, Oradell, N.J.; and in *Ocular Pharmacology*, by Havener, Chapter 15, 1978, published by C.V. Mosby Co., St. Louis; and in *Remington' Pharmaceutical Sciences*, 14th Ed., pages 886 to 899, 1970, published by Mack Publishing Co., Easton, Penna. While, the invention has been described and pointed out in detials, as applied to preferred embodiments, those skilled in the art will appreciate that various modifications, changes and omissions in the ocular delivery program described can be made without departing from the spirit of the invention.

We claim:

1. A topically applied composition for treating inflammation of a warm-blooded animal afflicted with same, wherein the composition comprises: a pair consisting essentially of two topically acceptable different physical and chemical therapeutic forms of the same steroid, the pair selected from the group consisting essentially of prednisolone, prednisolone acetate, prednisolone trimethylacetate, prednisolone hemisuccinate, prednisolone phosphate, prednisolone valerate, prednisolone propionate, prednisolone butyrate, prednisolone phenylacetate, 16α-methyl-16α-fluoroprednisolone, 16α-methyl-6α-fluoroprednisolone acetate, 16α-methyl-6α-fluoroprednisolone disodium phosphate, prednisolone-21-N, N-dimethylglycinate, and prednisolone-21-N, N-diethylglycinate, said compositon containing from 0.01% to 10% of each therapeutic form of the same steroid comprising the pair, said pair comprising both forms present in a bioerodible polymeric polyorthoester topical carrier without any interactions, and wherein when the composition is administered topically, the composition administers the steriods by the polyorthoester bioeroding and administering the two different forms as a pair, for increasing the concentration of each steroid for topically, with the concentration of each steroid form topically applied being independent of the amount of the different steroid form topically applied from the polyorthoester for increasing the concentration of each steroid form available for passing into the tissues and steroid receptors of a warm-blooded animal in a therapeutically effective amount for treating inflammation over a prolonged period up to 600 hours.

2. A topically applied composition for treating inflammation of a warm-blooded animal afflicted with same, wherein the composition comprises: a pair of steroids consisting essentially of two topically acceptable different physical and chemical therapeutic forms of the same steroid, the pair selected from the group consisting essentially of prednisone, prednisone acetate, meprednisone, meprednisone acetate, chloroprednisone, and chloroprednisone acetate, said composition containing from 0.01% to 10% of each therapeutic form of the same steroid housed in a bioerodible, polymeric hydrophobic polyorthoester carrier, with both forms present in the bioerodible polyorthoester carrier without any interactions, and wherein when the composition is administered topically, the composition administers the steriods by the polyorthoester bioeroding and administering the two different forms as a pair for increasing the concentration of each steroid form topically with the concentration of each steriod form topically applied being independent of the amount of the different steroid form topically applied for increasing the concentration of each steroid form available for passing into the tissues and steroid receptors of a warm-blooded animal in a therapeutically effective amount for treating inflammation over a prolonged period of time up to 600 hours.

3. A topically applied composition for treating inflammation of a warm-blooded animal afflicted with same, wherein the composition comprises: a pair of steroids consisting essentially of two topically acceptable different physical and chemical therapeutic forms of the same steroid, the pair selected from the group consisting essentially of triamcinolone, triamcinolone acetate, trimacinolone diacetate, triamcinolone hexacetonide, triamcinolone acylate, descinolone, and descinolone acetonide, and a bioerodible, polymeric hydrophobic polyorthoester carrier containing from 50 nanograms to 1 gram of each therapeutic form of the steroid pair, with both forms present in the bioerodible polyorthoester carrier without any interactions, and wherein when the composition is administered topically, the composition administers the steroids by the polyorthoester bioeroding and administering the two different forms as a pair, for increasing the concentration of each steroid form topically, with the concentration of each steroid form topically applied being independent of the amount of the different steroid form topically applied for increasing the concentration of each steroid form available for passing into the tissues and the steroid receptors of a warm-blooded animal in a therapeutically effective amount for treating inflammation over a prolonged period of time up to 600 hours.

4. A topically applied composition for treating topical inflammation and topical diseases of a warm-blooded animal afflicted with same, wherein the composition comprises: a pair of steroids consisting essentially of two topically acceptable different physical and chemical therapeutic forms of the same steroid, the pair selected from the group consisting essentially of fluorometholone, fluorometholone acetate, flurandrenolone, flurandrenolone ester, clocortolone acetate, and clocortolone, and a topically bioerodible, polymeric hydrophobic polyorthoester carrier containing from 50 nanograms to 1 gram of each therapeutic form of the steroid pair, with both forms present in the bioerodible polyorthoester carrier without any interactions, and wherein when the composition is administered topically, the composition administers the steroids by the polyorthoester bioeroding topically and administering the two different forms as a pair, for increasing the concentrations of each steroid form topically, with the concentration of each steroid form topically applied being independent of the amount of the different steroid form topically applied for increasing the concentration of each steroid form available for passing into the tissues and steroid receptors of a warm-blooded animal in a therapeutically effective amount for treating the inflammation and diseases responsive to the steroid pair over a prolonged period of time up to 600 hours.

5. A topically administered composition for treating inflammation and diseases responsive to steroid therapy, the composition topically administered to a warm-blooded animal afflicted with same, wherein the composition comprises: a pair of steroids consisting essentially of two topically acceptable different physical and chemical therapeutic forms of the same steroid, the pair selected from the group consisting essentially of formocortol, formocortol ester, fluperolone, fluperolone acetate, fluocinonide, fluocinonide acetate, fluocinonide ester, flunisolide, flunisolide acetate, flucloronide, and flucloronide ester, and a bioerodible polymeric polyorthoester carrier containing from 50 nanograms to 1 gram of each therapeutic form of the steroid pair, with both forms present in the bioerodible polyorthoester carrier without any interactions, and wherein when the composition is administered topically, the composition administers the steriods by the polyorthoester bioeroding topically in a therapeutically effective amount for treating inflammation and diseases over a prolonged period of time up to 600 hours.

6. A topically administrable composition for treating inflammation and topical diseases of a warm-blooded animal afflicted with same, wherein the composition comprises: a pair of steroids consisting essentially of two topically acceptable different physical and chemical therapeutic forms of the same steroid, the pair selected from the group consisting essentially of dichlorisone, dichlorisone acetate, difluprednate acetate, difluprednate butyrate, desoximetasone, and desoximetasone acetate, and a topically administrable, bioerodible polymeric polyorthoester carrier containing from 50 nanograms to 1 gram of each therapeutic form of the steroid pair, with both forms present in the bioerodible polyorthoester carrier without any interactions, and wherein when the composition is administered topically, the polyorthoester bioerodes topically and administers the two different forms as a pair, for increasing the concentration of each steroid form topically, with the concentrations of each steroid form topically applied being independent of the amount of the different steroid form topically applied for increasing the concentration of each steroid form available for passing into the tissues and steroid receptors of a warm-blooded animal in a therapeutically effective amount for treating the inflammation and topical diseases responsive to the steroid pair over a prolonged period of time up to 600 hours.

* * * * *